(12) United States Patent
Soloway (10) Patent No.: US 7,748,383 B1
(45) Date of Patent: Jul. 6, 2010

(54) AIR FILTERS

(76) Inventor: Michael S. Soloway, 30 Cresta Pequeno, Santa Fe, NM (US) 87505

( * ) Notice: Subject to any disclaimer, the term of this patent is extended or adjusted under 35 U.S.C. 154(b) by 1411 days.

(21) Appl. No.: 10/176,199

(22) Filed: Jun. 19, 2002

(51) Int. Cl.
*A61M 11/00* (2006.01)
(52) U.S. Cl. .............................. 128/206.11
(58) Field of Classification Search ........... 128/206.11, 128/206.18, 207.13, 207.18, 848, 858; 606/161, 606/162, 198, 199, 204.45
See application file for complete search history.

(56) References Cited

U.S. PATENT DOCUMENTS

| | | | | | |
|---|---|---|---|---|---|
| 1,311,461 | A | * | 7/1919 | Reynard | 128/203.22 |
| 1,322,375 | A | * | 11/1919 | Un | 128/206.11 |
| 1,474,710 | A | * | 11/1923 | Grier | 128/203.22 |
| 2,162,583 | A | * | 6/1939 | Kjellsson | 128/206.11 |
| 2,771,021 | A | | 11/1956 | Buckley | 98/87 |
| 2,890,695 | A | * | 6/1959 | Safstrom | 128/206.11 |
| 2,988,169 | A | | 6/1961 | Klein | 183/49 |
| 3,463,149 | A | * | 8/1969 | Albu | 128/204.12 |
| 3,698,308 | A | | 10/1972 | Navara | 98/99 |
| 3,747,597 | A | * | 7/1973 | Olivera | 128/206.11 |
| 3,802,426 | A | * | 4/1974 | Sakamoto | 128/206.11 |
| 3,826,182 | A | | 7/1974 | Navara | 98/98 |
| 3,905,335 | A | | 9/1975 | Kapp | 128/140 |
| 3,941,034 | A | | 3/1976 | Helwig et al. | 98/2.11 |
| 4,030,491 | A | * | 6/1977 | Mattila | 128/206.11 |
| 4,042,357 | A | | 8/1977 | Gysi | 55/417 |
| 4,052,983 | A | * | 10/1977 | Bovender | 128/204.12 |
| D251,017 | S | | 2/1979 | Amezcua | 24/99 |
| 4,220,150 | A | * | 9/1980 | King | 128/206.11 |
| 4,221,217 | A | * | 9/1980 | Amezcua | 128/206.11 |
| 4,267,831 | A | * | 5/1981 | Aguilar | 128/203.14 |
| 4,327,719 | A | * | 5/1982 | Childers | 128/206.11 |
| 4,370,155 | A | * | 1/1983 | Armbruster | 96/140 |
| 4,401,117 | A | * | 8/1983 | Gershuny | 128/206.11 |
| 4,457,756 | A | * | 7/1984 | Kern et al. | 604/286 |
| 4,573,461 | A | * | 3/1986 | Lake | 128/201.18 |
| 4,955,945 | A | * | 9/1990 | Weick | 128/203.12 |
| 5,350,444 | A | | 9/1994 | Gould | 96/154 |
| 5,417,205 | A | | 5/1995 | Wang | 128/206.11 |
| 5,472,379 | A | | 12/1995 | Andress et al. | 454/158 |
| 5,525,145 | A | | 6/1996 | Hodge | 96/17 |
| 5,554,205 | A | | 9/1996 | Ernst et al. | 55/385 |
| 5,568,808 | A | * | 10/1996 | Rimkus | 128/206.11 |
| 5,690,719 | A | | 11/1997 | Hodge | 96/17 |
| 5,776,218 | A | | 7/1998 | Enns | 55/495 |
| 5,890,491 | A | * | 4/1999 | Rimkus | 128/206.11 |
| 6,205,016 | B1 | * | 3/2001 | Niu | 361/503 |
| 6,213,121 | B1 | * | 4/2001 | Cardarelli | 128/206.18 |
| 6,216,694 | B1 | * | 4/2001 | Chen | 128/206.11 |
| RE37,150 | E | | 5/2001 | Anonychuk | 55/385 |
| 6,293,860 | B1 | | 9/2001 | Kim | 454/155 |
| D451,193 | S | | 11/2001 | McCormick | D24/106 |
| 6,395,046 | B1 | * | 5/2002 | Emig et al. | 55/382 |
| 6,752,149 | B2 | * | 6/2004 | Gillespie et al. | 128/204.12 |
| 6,971,387 | B2 | * | 12/2005 | Michaels | 128/206.11 |
| 2003/0106555 | A1 | * | 6/2003 | Tovey | 128/205.27 |

* cited by examiner

*Primary Examiner*—Steven O Douglas
(74) *Attorney, Agent, or Firm*—Franklin & Associates International LLC; Matthew F. Lambrinos (57) ABSTRACT

Air filters for use in nostrils, building structures and vehicles. The air filter is washable, reusable, non-toxic, and, for nostrils, comfortable to wear. It filters or stops allergens, while allowing airflow.

7 Claims, 7 Drawing Sheets

AIR FILTERS

BACKGROUND OF THE INVENTION

The present invention is directed to air filters, including their manufacture and use. The air filters of the present invention comprise a washable, non-toxic material that filters, hooks and removes allergy pollens, primary dust and other airborne allergens and irritants while allowing continuous and unrestricted airflow through the material.

DESCRIPTION OF THE PRIOR ART

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Nose Filters

The following references are directed to nose filters. None of them disclose a washable and reusable filter. This is particularly important if the user has a sinus or cold condition.

U.S. Pat. No. 3,463,149, to Albu, entitled "Nose Air Filter," discloses a nose plug system connected by a plastic or metal wire. However, it is made out of cotton filler with a porous fabric cover and is not washable. Some people are allergic to certain fabric materials and cotton and it may exacerbate allergies.

U.S. Pat. No. 5,890,491 to Rimkus, entitled "Nose Filter," discloses a disposable nose filter, including a flexible housing, a filtering component, a flange and an adhesive component. It is not washable or reusable. In the present invention, there is not any adhesive component and the filter is washable and reusable.

The following patents disclose cartridge systems, which are not washable: U.S. Pat. No. 3,905,335, to Kapp, entitled "Nasal Air Filter"; U.S. Design Pat. No. 251,017, to Amezcua, entitled "Nasal Device"; U.S. Pat. No. 4,052,983, to Bovender, entitled "Nasal Filter", and U.S. Pat. No. 5,417,205, to Wang, entitled "Air Filter for the Nose." Many of these systems are quite complex, and appear to be very uncomfortable.

In contrast, the nose filter of the present invention is washable, reusable, comfortable, flexible, non-toxic and non-allergenic.

Vehicle Filters

The following automotive or vehicle filters are all directed to automotive filters, none of which disclose a washable, reusable filter: U.S. Pat. No. 6,293,860 to Kim, entitled "Motor-Vehicle Passenger-Compartment Air-Cleaner"; U.S. Pat. No. RE37,150 to Anonychuk, entitled "Occupant Air Filter for Vehicles"; U.S. Pat. No. 5,554,205 to Ernest, et al., entitled "Air Filter for the Interior of a Motor Vehicle"; U.S. Pat. No. 5,472,379 to Andress et al., entitled "Air Filter for the Interior of Motor Vehicles"; U.S. Pat. No. 3,941,034 to Helwig et al., entitled "Filter Attachment for Automobile Passenger Compartment Air Intake"; and U.S. Pat. No. 5,350,444 to Gould et al., entitled "Passenger Vehicle with a Filtered Air Intake."

In contrast, the automotive filter of the present invention provides a reusable and washable filter for use in vehicles.

Window/Door/Skylight/Tent Filters

The following patents disclose filters used in buildings, none of which are washable and reusable: U.S. Pat. No. 2,771,021 to Buckley, entitled "Door with Built-In Deordorizer'" U.S. Pat. No. 3,698,308 to Navara, entitled "Filter System for Windows"; U.S. Pat. No. 3,826,182 to Navara, entitled "Window Air Filter with Locking Assembly"; and U.S. Pat. No. 4,042,357 to Gysi, entitled "Air Filter Unit for Sliding Sash Windows."

In contrast, the filters of the present invention, particularly useful for windows, doors and skylights of permanent and non-permanent (e.g., tents) structures or buildings, are washable, reusable and replaceable.

Heating and Cooling Filters

The following patents are directed for filters used with heating or cooling systems, none of which are removable, washable or replaceable: U.S. Pat. No. 5,525,145, to Hodge, entitled "Filtering Apparatus for a Forced Air Duct Grill"; U.S. Pat. No. 5,690,719, to Hodge, entitled "Removable Filter for a Forced Air Duct Grill"; and U.S. Pat. No. 5,776,218, to Enns, entitled "Duct Insertion Filter".

In contrast the heating/cooling filter of the present invention is washable, removable, replaceable and non-toxic.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

SUMMARY OF THE INVENTION

The present invention is of a nose filter comprising: at least one nostril plug comprising a filter material comprising openings of a size sufficient for passage of air, the openings further comprising a size smaller than particles to be filtered, the particles selected from the group consisting of allergens, dust, and toxins; the plug being washable and reusable for reinsertion of the plug into the nostril; and the plug being flexible for providing comfort for the nostril. In the preferred embodiment, two nostril plugs are employed with a bridge disposed therebetween. Each of the plugs preferably comprises an outer material and an inner filter material, with the outer material comprising a gel material and/or a clear polymer, and the inner filter material comprising a fabric material.

The invention is also of a vehicle filter comprising: a filter comprising openings of a size sufficient for passage of air, the openings further comprising a size smaller than particles to be filtered, the particles selected from the group consisting of allergens, dust, and toxins, the filter being washable and reusable for reinsertion of the filter into the vehicle; and a mount for disposing the filter in the vehicle. In the preferred embodiment, a cover is placed over the filter. The filter may be mounted inside the vehicle, such as on the dashboard, or mounted inside the engine compartment.

The invention is additionally of a building structure filter comprising: at least one filter material comprising openings of a size sufficient for passage of air, the openings further comprising a size smaller than particles to be filtered, the particles selected from the group consisting of allergens, dust, and toxins, the filter material being washable and reusable for reinsertion of the filter material into a building structure; and a mount for the filter material. In the preferred embodiment, the filter is mounted in a window opening, a door opening, a skylight opening, or a tent opening, or in a heating system, a cooling system, a heating/cooling system, or in an air supply system.

It is a primary object of the present invention to provide an air filter that is washable, reusable and replaceable.

It is a further object of the present invention to provide an air filter for a variety of common uses.

A primary advantage of the present invention is that it is inexpensive to manufacture, and easy to wash and replace.

It is a further advantage of the present invention to provide a nose filter that is comfortable and easy to wear.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

DESCRIPTION OF THE PREFERRED
EMBODIMENTS OF THE INVENTION

The present invention is directed to air filters, for a variety of uses. Possible applications are discussed below.

Nose and Sinus Air Filter

The present invention provides a nose filter, useful for filtering out allergens, toxins and chemicals, odors, and even providing protection against heat and cold.

Figure 1:
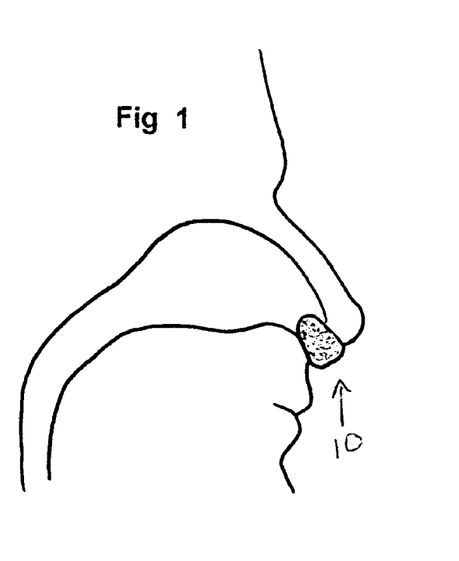
FIG. 1 shows a side view of a preferred nose filter embodiment of the present invention, inserted into a nostril.
Figure 2:
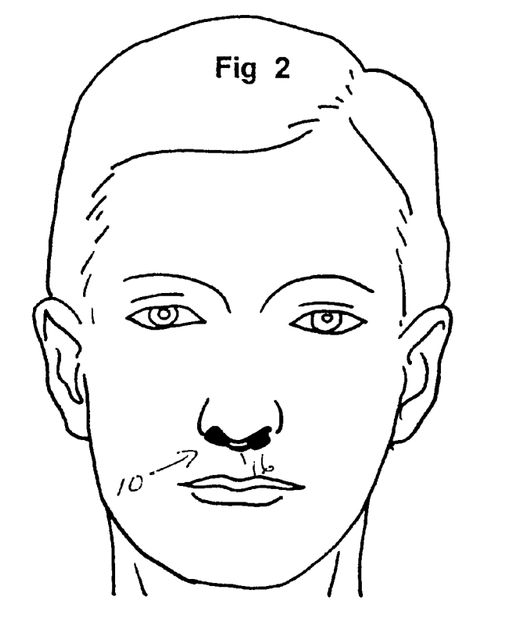
FIG. 2 shows a front view of the FIG. 1 nose filter embodiment, inserted into both nostrils.
Figure 3:
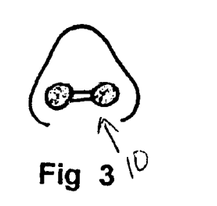
FIG. 3 shows an end view of the FIG. 1 nose filter embodiment showing the nose filter inserted into both nostrils.
Figure 4:
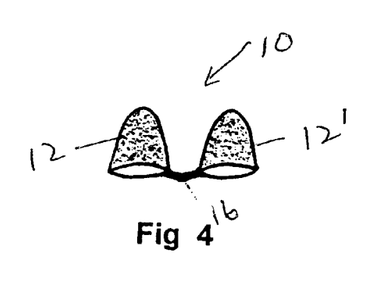
FIG. 4 shows a side perspective view of the FIG. 1. nose filter embodiment.

As shown in FIGS. 1-4, the nose filter of the present invention comprises a washable, reusable and non-toxic nose filter piece 10 inserted into both nostrils simultaneously (see FIGS. 2 and 3). Two individual filter nose plugs 12,12' are seated on and/or within a clear, soft holding gel or flexible polymer base (see FIG. 4) which allows for easy insertion and removal from the nostrils of the nose (see FIG. 3). The flexible polymer base is manufactured in various sizes (e.g., three sizes) to allow for use in small, medium and large size nostrils (e.g., children, adult female and adult male).

The nose filter may comprise individual plugs 12,12' which must be inserted nostril by nostril. Preferably, plugs are connected by bridge 16 to allow for simultaneous insertion into the nostrils. Also, bridge helps prevent plugs 12,12' from getting lost during washing. Bridge may comprise plastic, string, wire, fabric, rubber or other elastic material, and the like, so long as it is washable with nose plugs or removable from nose plugs prior to washing.

The filter is preferably cylindrically shaped, or nostril shaped to provide a soft seal within the inner nostril membrane. The filter fabric directs fresh air through the filtering material and at the same time prevents air from passing between the filter and the inner walls and membrane of the nostrils (see FIG. 1). The nose filter piece can be removed, washed and reinserted with ease by the user.

The preferred materials used in manufacture of the nose filter of the present invention are materials which provide micron or sub-micron airflow, while preventing large particles (e.g., allergens) from entering the nostrils. Useful materials in accordance with the present invention include natural and synthetic polymers, polyesters, rayon fibers, composites, solvent spun fibers, sub-micron or micron fabrics, and the like. Two manufacturing processes are presently preferred for developing nanofibers in a micron and sub-micron size suitable for the invention, namely "island in the sea" melt processing and electric spinning, but processes resulting in equivalent structures in the future are intended to be covered by the present invention.

Vehicle Interior Compartment Air Filter

Figure 5:
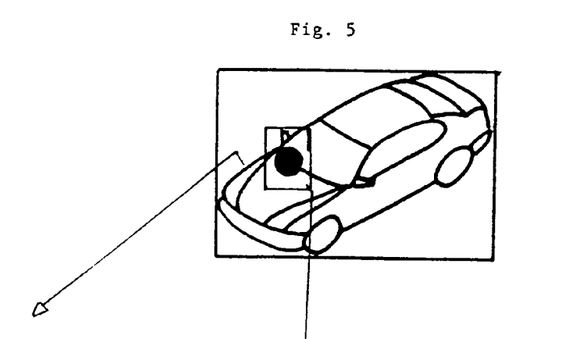
FIG. 5 shows a preferred automotive filter of the present invention, with its positioning in a vehicle.
Figure 6:
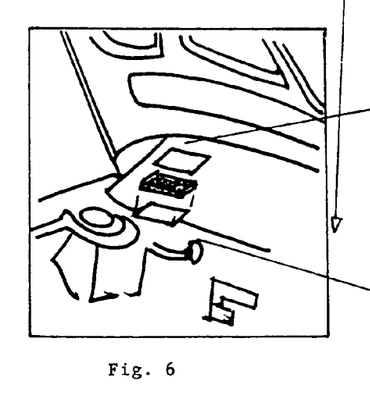
FIG. 6 shows an interior view of the vehicle and placement of the FIG. 5 filter.
Figure 7:
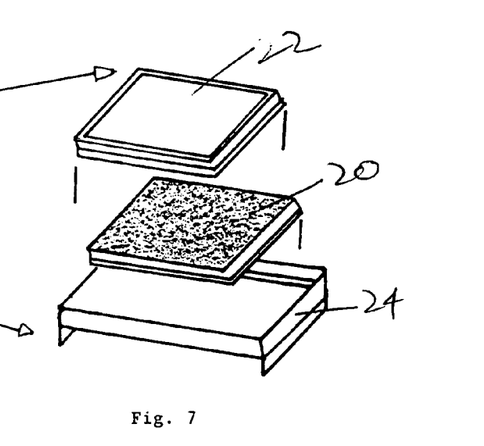
FIG. 7 shows an expanded perspective view of the filter and filter casings of the FIG. 5 embodiment.

As shows in FIGS. 5-7, the present invention also relates to a washable, reusable and non-toxic vehicle filter 20 that is used within a fresh air duct system of a vehicle (e.g., automobile, truck or other transportation vehicle) that supplies exterior air to the interior. Filter 20 may be provided to the passenger area or driver area. The filter is also useful in connection with the air conditioning feature of the vehicle.

Filter 20 is preferably placed within an existing filter channel or sleeve which is located under a hood of the vehicle or as part of or under the dashboard. Filter 20 is preferably encased or disposed between screen 22 and mount 24 to provide protection for and easy access to filter 20. Filter 20 may be manufactured in a variety of sizes to replace the disposable and non-reusable pleated polyester filters currently the standard in the automotive industry.

Vehicles may be manufactured with the filter system of the present invention. Alternatively, vehicles may retrofitted by installing a retrofit duct section that has a manufactured molded filter channel or sleeve 24 to securely hold the washable and non-toxic filter of the present invention.

Window-Door-Skylight Air Filtering Screen Material

Figure 8:
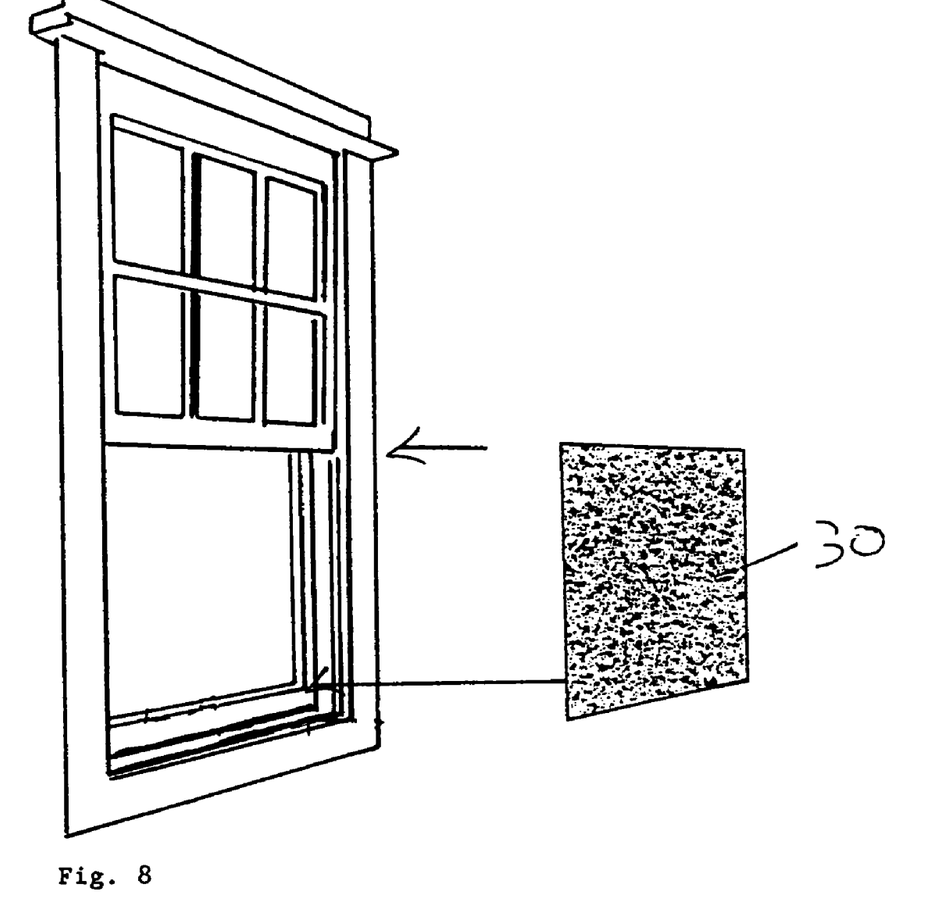
FIG. 8 shows a side perspective expanded view of a preferred window filter of the present invention, insertable into a window.
Figure 9:
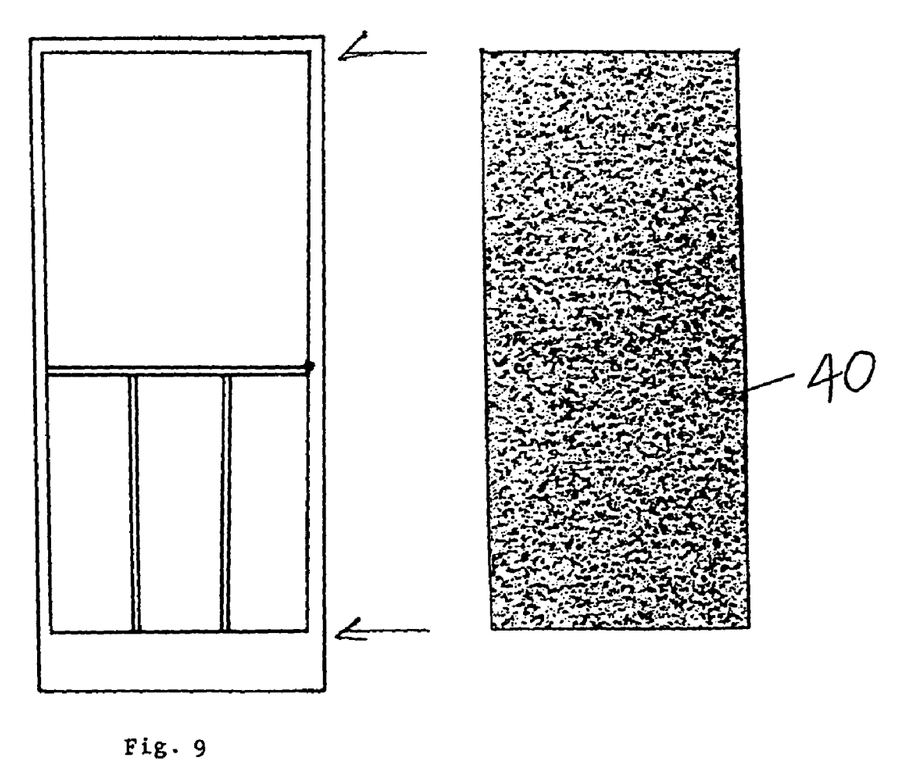
FIG. 9 shows a side expanded view of a preferred door filter of the present invention, insertable into a door.
Figure 10:
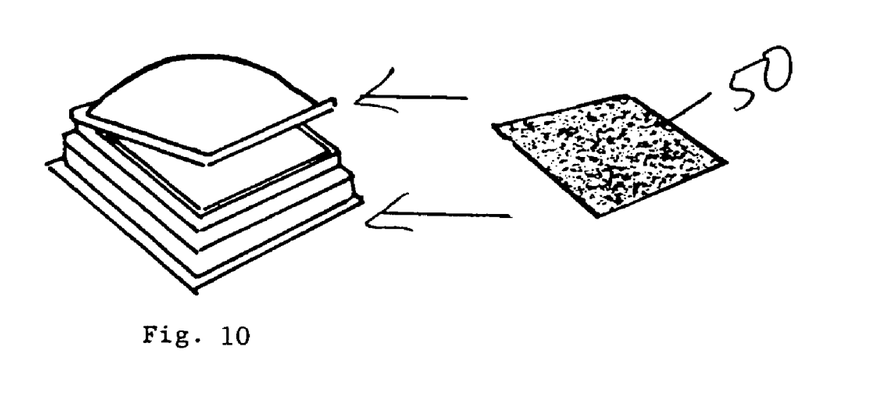
FIG. 10 shows a perspective expanded view of a preferred skylight filter of the present invention, insertable into a skylight.

The present invention also relates to a washable, reusable and flexible window, door or skylight screening material that filters incoming air into the residential home, commercial building or other structure (see FIGS. 8-10). The filtering material of the present invention replaces the prior art non-filtering woven polyester or aluminum screen material used, e.g., within the window industry.

FIG. 8 is directed to a window filter material 30. FIG. 9 is directed to a door filter material 40. FIG. 10 is directed to a skylight filter material 50. Framing for the screening/filter material of the present invention requires particular specifications in accordance with the dimensions of the particular window, door or skylight to eliminate any airflow drawn around instead of through the filtering screen material.

Older windows, doors and skylights are fitted with a retrofit filter/screen material of the present invention that is disposed on or attaches (e.g., clips) tightly into the existing window, door or skylight screen channel or frame.

The term "building structure" as used throughout the specification and claims, is intended to cover windows, doors, skylights, tents, heating systems, cooling systems, heating and cooling systems, air flow systems, and any other opening that provides air within a structural space.

Tent Air Filter Screening Material

Figure 11:
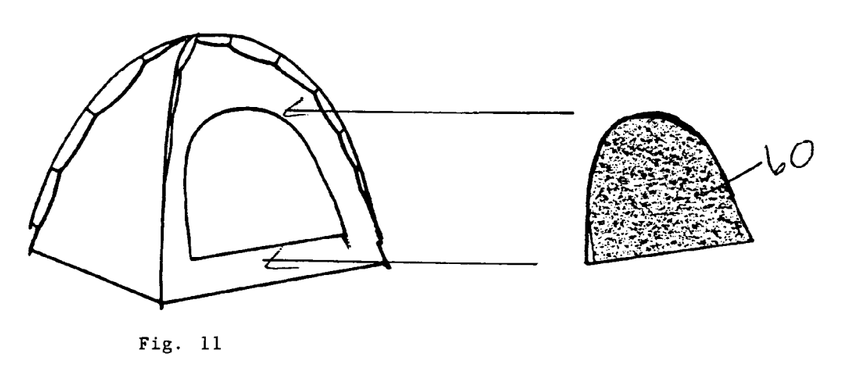
FIG. 11 shows a perspective expanded view of a preferred tent filter of the present invention, insertable into an opening of a tent.

As shown in FIG. 11, the present invention also relates to a washable, reusable, non-toxic and flexible screening fabric that is used within an open air window and door space areas of a tent. The filter screening material 60 is sewn into an existing window and door space opening of the tent or is attached (e.g., with the use of Velcro, hook and loop strips, frame, or the like).

Heating and Cooling Filter Screening Material

Figure 12:
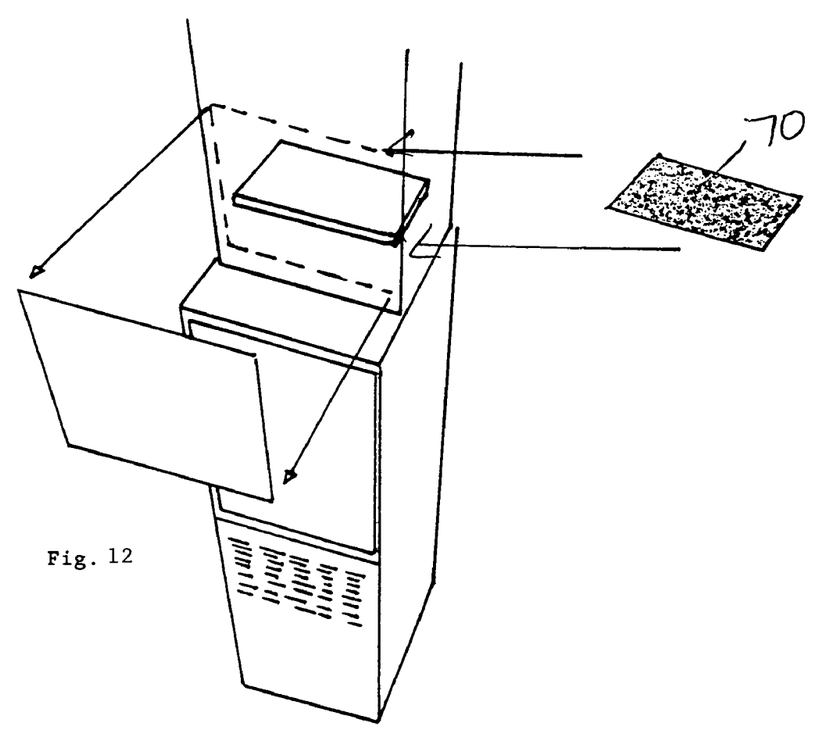
FIG. 12 shows a top perspective expanded view of a preferred heating/cooling filter of the present invention, insertable into an airflow conduit of a heating/cooling system.

The present invention also relates to a washable, reusable and non-toxic filter screening material that replaces existing non-reusable and disposable polyester filters in currently manufactured heating and cooling systems. As shown in FIG. 12, filter screening material 70 is used in conjunction with an air conditioner, evaporative cooler or forced air furnace unit, as well as all other industrial heating and cooling systems. Likewise, the filter may be used in air intake or supply systems, even if not connected to a heating or cooling system.

Materials

Useful materials for the filters of the present invention include materials which provide sub-micron or micron openings to allow for air flow, but stop allergens, toxins and the like, from passing through the filter. Useful materials in accordance with the present invention include natural and synthetic polymers, polyesters, rayon fibers, composites, solvent spun fibers, sub-micron or micron fabrics, and the like. Two manufacturing processes are presently preferred for developing nanofibers in a micron and sub-micron size suitable for the invention, namely "island in the sea" melt processing and electric spinning, but processes resulting in equivalent structures in the future are intended to be covered by the present invention. These resultant materials must be durable for handling and washing. These materials are washed by the user from time to time and then reused in their particular applications. Washing preferably removes most of the allergens or toxins collected during filtering.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A nose filter comprising:
    at least one nostril plug comprising a self supporting filter material comprising island-in-the-sea nano fibers in micron or sub-micron size, said filter material comprising micron or sub-micron openings and providing micron or sub-micron air flow whilst preventing particles from passing through said nose filter, said particles selected from the group consisting of allergens, dust, and toxins, said plug being washable and reusable for reinsertion of said plug into the nostril; and
    said plug being flexible for providing comfort for the nostril.

2. The nose filter of claim 1 comprising two nostril plugs, comprising a bridge disposed therebetween.

3. The nose filter of claim 1 wherein each of said plugs comprise an outer material and an inner filter material.

4. The nose filter of claim 3 wherein said outer material comprises a gel material.

5. The nose filter of claim 3 wherein said outer material comprises a clear polymer.

6. The nose filter of claim 3 wherein said inner filter material comprises a micron or sub-micron fabric material.

7. The nose filter of claim 1, wherein said filter material further comprises melt processed or electric spun nano fibers in micron or sub-micron size.

\* \* \* \* \*